United States Patent [19]
Hsu et al.

[11] Patent Number: 6,063,383
[45] Date of Patent: May 16, 2000

[54] PHARMACEUTICAL SUPPOSITORY COMPOSITES FOR FEVER AND INFLUENZA AND METHOD OF PRODUCING THE COMPOSITES

[76] Inventors: Wu-Ching Hsu; Su-Hsien Keng, both of No. 2, Alley 16, Lane 41, Sec. 2, Nan-Ching E. Rd., Taipei, Taiwan

[21] Appl. No.: 09/238,744

[22] Filed: Jan. 28, 1999

[51] Int. Cl.[7] .......................... A01N 25/00; A01N 65/00; A61K 35/78; A61K 39/385; A61K 47/00
[52] U.S. Cl. ....................... 424/195.1; 514/783; 514/849; 514/853; 514/888; 514/922
[58] Field of Search .................... 424/195.1; 574/783, 574/849, 853, 888, 922

[56] References Cited

U.S. PATENT DOCUMENTS 5,886,028   3/1999   Vallee et al. ............................ 514/456

Primary Examiner—Leon B. Lankford, Jr.
Assistant Examiner—Deborah K. Ware
Attorney, Agent, or Firm—Bacon & Thomas

[57] ABSTRACT

Pharmaceutical suppository composites for fever and influenza and method of producing them, therefore, are disclosed herein. More particularly, the composites combine all the advantages of traditional Chinese medicine, western medicine, and physical temperature reduction to relieve symptoms of influenza. Poisonous side effects can be avoided by using the disclosed suppositories. The pharmaceutical suppository composites comprise 2,750 g to 3,250 g radix bupleuri scorzonerifolium wild, 1,750 g to 2,250 g flos lonicerae japonicae, 1,950 g to 2,450 g fructus forsythiae, 1,650 g to 2,150 g fructus arctii, 2,550 g to 3,050 g herba schizonepetae, 50 g to 550 g calculus bovis and 870 g to 1,370 g of excipients.

37 Claims, 6 Drawing Sheets

Fig. 1

| Group | Dosage (g/kg) | Basal Body Temperature (°C) | Before Medication (°C) | After Medication | | | | |
|---|---|---|---|---|---|---|---|---|
| | | | | 1hr | 2hr | 3hr | 4hr | 5hr |
| Excipient | — | 37.8±0.36 | 39.1±0.40 | 39.2±0.32 | 39.2±0.42 | 39.1±0.44 | 39.0±0.37 | 38.7±0.49 |
| Children's antipyretic suppository | 0.16 | 37.8±0.33 | 39.2±0.39 | 38.9±0.41 | 38.6±0.44 ** | 38.6±0.45 * | 38.6±0.45 * | 38.5±0.41 |
| Suppository for fever and influenza | 2 | 37.7±0.33 | 39.1±0.36 | 38.9±0.38 | 38.7±0.40 * | 38.6±0.38 ** | 38.5±0.41 ** | 38.3±0.38 |
| Suppository for fever and influenza | 4 | 37.8±0.34 | 39.2±0.36 | 38.8±0.41 * | 38.5±0.42 ** | 38.4±0.53 ** | 38.4±0.48 ** | 38.1±0.42 |

Note: *$P<0.05$  **$P<0.01$  △$P<0.05$

Fig. 2

| Group | Dosage (g/kg) | No. of Animals | Weight Change(g, X+/−SD) | | | Performance after medication |
|---|---|---|---|---|---|---|
| | | | Before medication | 24 hrs after medication | 7 days after medication | |
| Excipient Control | — | 10 | 254.0 ± 12.0 | 254.7 ± 13.31 | 273.7 ± 13.3 | Move freely; its reactions are normal; respiratory stable; feces in shape; lustrous hairs |
| Suppository for fever and influenza | 6 | 10 | 253.2 ± 10.6 | 253.5 ± 10.5 | 273.1 ± 11.7 | After medication, activites of wister rats appear to reduce, and then restore to the normal activity level; the others are same as the above. |
| Suppository for fever and influenza | 12 | 10 | 252.9 ± 11.3 | 253.1 ± 11.4 | 272.3 ± 11.0 | Same as the low-dosage group |

Fig. 3

| Date | Name | Age | Sex | Dosage | Before Medication | | Temp. after medication | | | Symptoms after medication | Ward | Bed No. |
|---|---|---|---|---|---|---|---|---|---|---|---|---|
| | | | | | Temp | Symptoms | 30' | 60' | 90' 120' | | | |
| 96 5/1 | Kuo Wen | 5 | F | 1/2 | 39.8 | Facial Redness, Convulsion | 39.8 | 38.2 | 37.4 36.5 | Symptoms alleviated | Pediatric | 2 |
| 96 17/1 | Wang hsiao-hung | 1½ | F | 2/3 | 38.5 | Coughing, Restlessness | 38.5 | 38.6 | 37.6 36.4 | Symptoms Disappeared | Pediatric | 6 |
| 96 28/1 | Liu Lei | 5 | M | 1/2 | 39.2 | Redness in the face, Restlessness | 38.4 | 36.2 | 37.4 36.8 | Symptoms Disappeared | Pediatric | 12 |
| 96 8/4 | Lee Chia-chia | 8 | M | 2/3 | 38.4 | Trembling, headache | 38.4 | 37.8 | 37.6 37.2 | Symptoms alleviated | Pediatric | 8 |
| 96 29/4 | Kuo Shan | 10 | F | 2/3 | 39.1 | Trembling, pain all over the body | 38.5 | 36.2 | 37.4 36.8 | Symptoms alleviated | Pediatric | 10 |
| 96 3/6 | Liu Hsiao-Li | 5 | F | 1/2 | 38.5 | Redness in the face, coughing | 37.4 | 36.8 | 37.2 36.5 | Symptoms alleviated | Pediatric | 13 |
| 96 27/6 | Sung Hsiao-Chun | 4 | M | 1/2 | 38.8 | Redness in the face Pains all over the body | 37.9 | 38.2 | 37.2 36.8 | Symptoms alleviated | Pediatric | 7 |
| 96 2/7 | Li Fei-Fei | 8/12 | M | 1/2 | 38.2 | Redness in the face, Restlessness | 37.2 | 38.1 | 37.1 36.6 | Symptoms alleviated Noticeably | Pediatric | 9 |
| 96 17/7 | Tien Yuan-Yuan | 2 | M | 1/2 | 38.4 | Coughing, crying | 37.8 | 36.9 | 37.2 36.4 | Symptoms alleviated Noticeably | Pediatric | 1 |
| 96 6/8 | Chung Chung | 2½ | M | 1/2 | 39.2 | Redness in the face, crying | 38.8 | 38.2 | 37.4 36.8 | Symptoms alleviated Noticeably | Pediatric | 5 |

Fig. 4

| Date | Name | Age | Sex | Dosae | Before Medication | | Temp. after medication | | | | Symptoms after medication | Ward | Bed No. |
|---|---|---|---|---|---|---|---|---|---|---|---|---|---|
| | | | | | Temp | Symptoms | 30' | 60' | 90' | 120' | | | |
| 96 8/1 | Meng Lien | 9/12 | M | 1/2 | 39.8 | Facial Redness, Convulsion | 39.8 | 39.2 | 38.7 | 38.1 | Symptoms alleviated | Pediatric | 10 |
| 96 10/1 | Wang Ching | 3 | F | 2/3 | 40.8 | Shortness in breath | 40.5 | 39.2 | 38.1 | 37.2 | Symptoms Disappeared | Pediatric | 8 |
| 96 13/1 | Chang Wen-Cheng | 2 9/12 | M | 2/3 | 39.4 | Redness in the face | 38.2 | 37.1 | 36.4 | 36.4 | Symptoms Disappeared | Pediatric | 6 |
| 96 16/1 | Sun Fei | 3 | M | 2/3 | 38.7 | Redness in the face | 38.5 | 37.2 | 37.3 | 36.5 | Symptoms alleviated | Pediatric | 7 |
| 96 1/2 | Chang Yeh | 2 | M | 2/3 | 39 | Redness in the face, coughing | 38.2 | 38.1 | 37.2 | 36.5 | Symptoms alleviated | Pediatric | 2 |
| 96 9/2 | Wang Ching | 2 6/12 | F | 2/3 | 37.7 | Redness in the face, coughing | 37.2 | 36.5 | 36.2 | 36.4 | Symptoms alleviated | Pediatric | 5 |
| 96 19/2 | Chao Kuang-Fang | 3 | F | 2/3 | 37.8 | Shortness in breath | 37.5 | 36.8 | 36.2 | 36.3 | Symptoms alleviated | Pediatric | 13 |
| 96 8/3 | Ni Chen | 3 1/12 | M | 1/2 | 38.2 | Redness in the face, coughing | 37.9 | 37.5 | 36.8 | 36.2 | Symptoms Disappeared | Pediatric | 12 |
| 96 9/3 | Liu Ching | 1 4/12 | M | 1/2 | 39 | Coughing, convulsion | 38.2 | 37.8 | 36.8 | 36.2 | Symptoms Disappeared | Pediatric | 11 |
| 96 20/3 | Yu Hung | 2 | F | 2/3 | 38.9 | Redness in the face, coughing | 38.5 | 37.9 | 37.4 | 36.8 | Symptoms Disappeared | Pediatric | 4 |

Fig. 5

| Date | Name | Age | Sex | Dosage | Before Medication | | Temp. after medication | | | | Symptoms after medication | Ward | Bed No. |
|---|---|---|---|---|---|---|---|---|---|---|---|---|---|
| | | | | | Temp | Symptoms | 30' | 60' | 90' | 120' | | | |
| 96 3/1 | Pai Tung | 51 | M | 1 | 38.5 | Trembling | 38.2 | 37.2 | 36.4 | 36.5 | Symptoms alleviated | Tumor | 9 |
| 96 12/1 | Liu Hsiu-ling | 33 | F | 1 | 39.3 | Headache | 38.5 | 37.7 | 37.5 | 36 | Symptoms alleviated | Tumor | 46 |
| 96 23/1 | Sun Yu-Ying | 59 | F | 1 | 40.2 | No noticeable symptoms | 40 | 39 | 38.1 | 37 | Symptoms alleviated | Tumor | 42 |
| 96 1/2 | Sun Yu-Ying | 59 | F | 1 | 39.8 | No noticeable symptoms | 38.5 | 37.8 | 36.8 | 36.4 | Symptoms alleviated | Tumor | 42 |
| 96 8/2 | Sun Ching | 40 | M | 1 | 38.5 | No noticeable symptoms | 37.6 | 37.5 | 36.6 | 36.4 | Symptoms alleviated | Tumor | 40 |
| 96 9/2 | Fan Hung | 37 | F | 1 | 38.8 | No noticeable symptoms | 38.2 | 37.6 | 36.8 | 36.5 | Symptoms alleviated | Tumor | 19 |
| 96 10/3 | Liu Hsiu-Ling | 33 | F | 1 | 39 | Pains all over the body | 38.9 | 38.4 | 38.2 | 37.1 | Symptoms alleviated | Tumor | 46 |
| 96 17/3 | Sun Ching | 40 | M | 1 | 38.9 | No noticeable symptoms | 38.2 | 37.9 | 36.2 | 36.4 | Symptoms alleviated | Tumor | 40 |
| 96 23/3 | Liu Yu | 38 | F | 1 | 39 | Pains all over the body | 38.8 | 37.2 | 36.5 | 36.7 | Symptoms alleviated | Tumor | 15 |
| 96 28/3 | Fan Hung | 37 | F | 1 | 38.5 | No noticeable symptoms | 38.2 | 37.4 | 36.8 | 36 | Symptoms alleviated | Tumor | 19 |

Fig. 6

PHARMACEUTICAL SUPPOSITORY COMPOSITES FOR FEVER AND INFLUENZA AND METHOD OF PRODUCING THE COMPOSITES

BACKGROUND OF THE INVENTION

The present invention relates to the pharmaceutical composites of the suppository for fever and influenza and their pharmaceutical methods, more particularly, to an antipyretic and anti-influenza suppository, which combines all the advantages of traditional Chinese medicine, western medicine, and physical temperature reduction in an effort to expel all the weaknesses of traditional Chinese medicine, western medicine, and physical temperature reduction, and which can rapidly bring down fever and relieve symptoms of influenza with fewer poisonous and side effects, and which can be used safely and conveniently and is suitable for both sexes and people of all ages.

Influenza is a disease that is generally regarded as insignificant by people. In fact, influenza is a highly infectious viral illness, which produce a set of recognizable and common symptoms—fatigue, fever, running with tears, nasal congestion, headaches, dryness of throat, or sore throat. A large number of viruses can cause influenza. Influenza virus is extremely small in size and can enter the human body through the filter of nasal passages. Generally speaking, this filter can only catch larger bacteria. Viruses rapidly multiply in number and invade the nose and throat to produce common influenza symptoms, and sometimes, may cause complications such as pneumonia or bronchitis. If these symptoms are not properly treated, they may be fatal. In fact, influenza is a common illness not to be ignored.

Currently, antipyretic and anti-influenza medication in the market can be classified into three categories: (1) Chemical pharmaceuticals (western medicine); (2) natural pharmaceuticals (traditional Chinese medicine); (3) physical temperature reduction (anti-pyrexia). For western therapy, antibiotics are generally used to bring down fever; steroids are used to relieve nasal congestion; antihistamine is used to treat symptoms of influenza, supplemented by a large intake of water and taking more rest. Generally speaking, the advantages of western medicine rest on its relative rapid and definite effectiveness and convenience. The weaknesses of western medicine are the different levels of toxicity and side effects accompanied with it. Examples are the tolerance of illnesses caused by antibiotics, the toxicity of steroids to the human body, and the injury of chemical substances to the viscera. All these are the adverse poisonous and side effects commonly known by people. The above-mentioned chemical pharmaceuticals are not satisfactory in relieving and preventing fever and influenza. The common drug forms of chemical pharmaceuticals and medication for influenza are capsules, tablets, suppositories, oral liquors, and nasal sprays (drops).

For traditional Chinese medicine, diaphoretics are commonly used to treat and prevent fever and influenza. They are natural pharmaceuticals, which are intended to promote sweating and expel external evil. The effects of diaphoretics primarily consist of the following three aspects: (1) Sweating: External evil can be expelled through sweating. Sweating can also prevent the spread of the evil to the internal organs; (2) Relieving muscles: Muscle relief refers to the condition that the evil has already penetrated into a deeper level of the body in which sweating occurs, but the external symptoms have not yet been relieved. Therefore, it is necessary to relieve the symptoms of the muscles caused by exogenous factors and expel the evil caused by these exogenous factors; (3) Inducing rashes: Some diaphoretics can direct qi (vital energy) to the exogenous factors and induce rashes. Since external evil can be divided into cold evil and hot evil, the human body can also be divided into two kinds, namely, patients with symptoms showing the deficiency of vital energy to ward off diseases and patients with cases characterized by a high fever or disorders like stasis and constipation. Therefore, diaphoretics can also be divided into warm-natured diaphoretics (for external symptoms caused by the cold-wind evil), cold-natured diaphoretics (for external symptoms caused by the hot-wind evil), and healthy energy-supporting diaphoretics (for external symptoms caused by the external evil for those patients with a deficiency of vital energy). Traditional Chinese medicine is primarily offered in powder and decoction (liquor). Generally speaking, its advantages are that traditional Chinese medicine can be used safely with good therapeutic effects and a relatively lower level of toxicity and fewer side effects. Its weaknesses are its slower therapeutic effects and the inconvenience in taking it.

For the therapy of temperature reduction and expelling heat, there is the physical temperature reduction like cold therapy, alcohol bath therapy, and an enema of ice water. Its advantage is its safety whereas its weaknesses are its unstable therapeutic effects and the inconvenience in using it. Even though the above therapies are effective to a certain degree, there are still cases in which the body temperature does not decrease, but increases instead. Patients are against cold because of their high fever and cannot accept the cold therapy and the alcohol bath therapy, which are not used conveniently.

Concluding from the treatment for fever and influenza by the traditional Chinese medicine, western medicine, and physical temperature reduction, all these therapies have advantages and also weaknesses. Therefore, if there is a pharmaceutical, which can combine all the advantages of the traditional Chinese medicine, western medicine, and physical temperature reduction and expel all the weaknesses of the above-mentioned pharmaceuticals or methods, this will be an extremely meaningful invention for people's health care.

SUMMARY OF THE INVENTION

It is the objective of this invention to develop this suppository for fever and influenza by combining all the advantages of chemical pharmaceuticals (western medicine), traditional Chinese medicine to treat fever for common illnesses, expel heat, relieve symptoms of influenza (such as fever, coughing, headaches, nasal congestion, sore throat, running nose, sneezing, and aching pains all over the body), and physical temperature reduction in an effort to expel all the weaknesses of traditional Chinese medicine, western medicine, and physical temperature reduction. In other words, this invention is a suppository, which can rapidly bring down fever and relieve symptoms of influenza with a low level of toxicity and fewer side effects, and which can be used safely and conveniently and is suitable for both sexes and people of all ages.

In order to achieve the objective set forth, this invention selects the drug form to be a suppository, which is produced with the addition of exicipients after extracting pharmaceuticals, and which can prevent the pharmaceuticals from the damage of the pH value or enzymes in the stomach and intestines so that the pharmaceuticals can be directly absorbed into the rectum to prevent them from the damage of the enzymatic action of livers and reduce the toxicity or side effects of the pharmaceuticals to the livers. In this way, the pharmaceuticals are absorbed into the rectum, in which the interference of pharmaceuticals is lower and the action of pharmaceuticals will last longer than when tablets are orally administered. The administration of the suppository to the rectum is more convenient for patients or children who cannot swallow or who have a difficulty in swallowing pharmaceuticals.

BFIEF DESCRIPTION OF THE DRAWINGS

In order that the present invention may more readily be understood, the following description is given, merely by way of example with reference to the accompanying drawings, in which.

DETAILED DESCEIPTION OF THE PRDFFRRED EMBODIMENT

Figure 1:
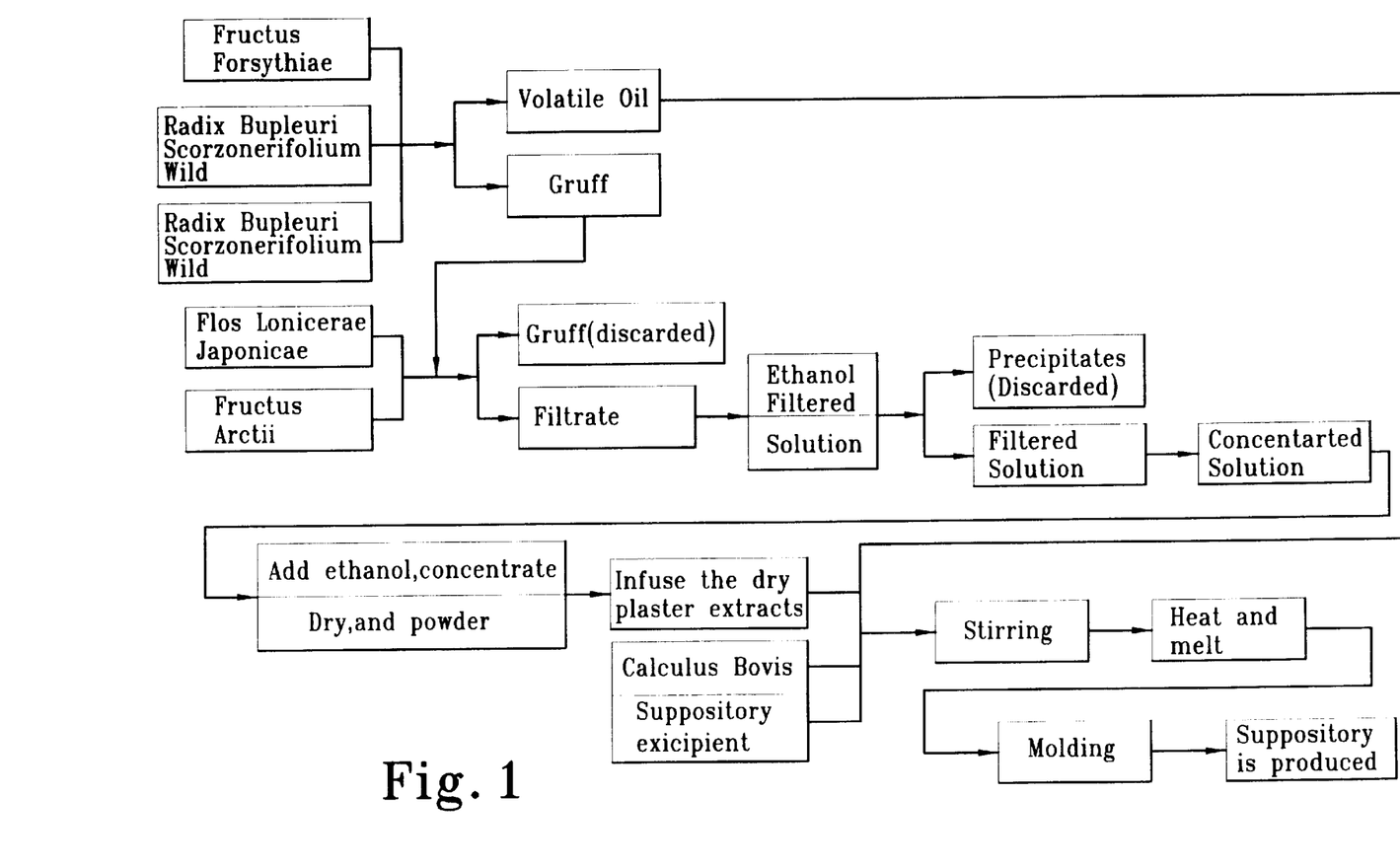
FIG. 1 is a schematic illustration of the pharmaceutical process of this invention.

Referring to the schematic illustration of the pharmaceutical process of this invention in FIG. 1, this suppository for fever and influenza is intended to directly provide influenza patients with pharmaceutical composites by directly administering the suppository to the rectum. Its pharmaceutical composites include 2,750 g. to 3,250 g. radix bupleuri scorzonerifolium wild, 1,750 g. to 2,250 g. flos lonicerae japonicae, 1,950 g. to 2,450 g. fructus forsythiae, 1,650 g. to 2,150 g. fructus arctii, 2,550 g. to 3,050 g. herba schizonepetae, 50 g. to 550 g. calculus bovis, and 870 g. to 1,370 g. suppository exicipients (for example, cocoa butter). This suppository is directly administered to the rectum so that it can be directly absorbed into the rectum so as to prevent it from the damage caused by the enzymatic action of livers, reduce the toxicity or side effects of the pharmaceuticals, and rapidly bring down fever and relieve symptoms of influenza (for example, fever, coughing, headaches, nasal congestion, sore throat, running nose, sneezing, and aching pains all over the body), accompanied with a little amount of toxicity and fewer side effects. It can be used safely and conveniently and is suitable for both sexes and people of all ages. The chemical composition, pharmacology, and effects of the above-mentioned pharmaceutical composites are stated as follows:

1. Radix Bupleuri Scorzonerifolium Wild:
Chemical Composition:

Its roots consist of a volatile oil, which contains $\beta$-terpinene, limonene, camphene, $\beta$-fenchene, pulegone, isoborneol, $\beta$-terpineol, linalool, $\alpha$-copaene, humulene, $\alpha$-farnesene, aromadendrene, cis-caryophyllene, iso-caryophyllene, $\beta$-elemene, $\gamma$-muurolene, patchoulane, nootkatone, and ledol. It also contains 0.15% Saikosaponin, which is made up of 0.05% bupleurum saponin-a, a little bupleurum saponin-d, and 0.10% bupleurum saponin-c. Its parts above the earth also contain ketones such as sorbitin, sorbiphenol-7-rhamnosin, quercetin, isoquercetin, isorhamnetin, rutin, and narcissin.

Pharmacology:

1. Anti-inflammation: An intra-abdominal injection of 478 mg/kg bupleurum saponin and 400 mg/kg bupleurum volatile oil has a significant inhibitory action on the swelling in the wister rats' feet caused by Chondrus ocellatus. Bupleurum saponin can inhibit the swelling in the wister rats' feet caused by dextrose anhydride, 5-HT, croton oil or acetic acid. Bupleurum saponin-a and bupleurum saponin-d have anti-osmosis (granulation implantation) and anti-granulomatous action (cotton granulomatous method). An intra-muscular injection of 50 mg/kg, 25 mg/kg 2% bupleurum saponin aqueous solution and 6% 0.1 mg/kg low-molecular dextrose anhydride can only inhibit the swelling of feet caused by dextrose anhydride. This inhibitory action increases with a higher dose. The anti-inflammation of 1.1 g/kg bupleurum decoction (ten times the quantity commonly consumed by people) for acute- and para-acute inflammation of wister rats is equivalent to that of 1 mg/kg prednisone. When bupleurum decoction is combined with 4 mg/kg prednisolne, the anti-inflammation of 16 mg/kg prednisolne is produced. Bupleurum saponin has an action on a lot of the inflammation processes such as osmosis, capillary permeability, the release of the inflammation medium, the drifting of white blood cells, and the proliferation of connectives. The removal of the two adrenal glands of wister rats has a significant inhibitory action on the osmosis of intra-abdominal secretion of wister rats caused by acetic acid. It is believed that its inflammation is related to the system of pituitary bodies-adrenal glands. After an intra-abdominal injection of 200 mg/kg bupleurum decoction has been administered, the corticosterone in serum and ACTH in plasma increase by five times and cAMP in pituitary bodies and adrenal glands increases by three times whereas no changes occur in the hypothalamus. This shows that besides the direct mechanism in which it directly acts on the inflammation parts, bupleurum decoction can also stop the inhibition of corticosterone on the secretion of ACTH, thus activating the anti-inflammation of the pituitary bodies-adrenal glands system for the swelling of feet of wister rats. When the bupleurum decoction is combined with cortin, the inflammation is greater than when only the cortin is used. This action is not only the summation of these two agents, but also increases the anti-inflammation of cortin. The buplerum, especially bupleurum saponin, in the bupleurum decoction has an agnostic effect on the anti-granulation action of steroids.

2. Action on the central nervous system:
   (1) Antipyretic action: After a rabbit has a fever after an intravenous injection of *Eschrichia coli.*, a hypodermic injection of a 5% aqueous solution of 2.42 g./kg (crude drugs) bupleurum falcatum extracts produces significant anti-pyrexia. A 20% 2 g/kg bupleurum falcatum decoction has a significant antipyretic effect on the rabbit's fever caused by expired mixed typhoid vaccine. When the decoction of the roots, stems, or leaves of bupleurum falcatum is injected into a rabbit's stomach, it can significantly reduce the rabbit's pyrexia caused by an intra-muscular injection of fermented milk. The antipyretic action of bupleurum falcatum root decoction is especially significant. It is believed that the roots of bupleurum falcatum contain a higher concentration of effective contents such as saponins and volatile oil than the stems or leaves of bupleurum falcatum. An oral medication of 800 mg/kg bupleurum saponin not only can reduce the wister rats' fever caused by the mixed typhoid and paratyphoid vaccine, but also reduce the normal body temperature of wister rats. Bupleurum saponin also has a significant antipyretic action. An intra-abdominal injection of 300 mg/kg ($\frac{1}{4}$ $LD_{50}$ bupleurum falcatum) volatile oil can significantly reduce wister rats' temperature rise caused by the suspension of cerevisiae fermentum.

(2) Tranquilizing and anti-convulsive action: Bupleurum saponin and bupleurum saponin-a have a significant tranquilizing effect. An oral administration of 200–800 mg/kg crude bupleurum saponin can produce a tranquilizing effect on small rats. The mounting experiments of small rats and the conditional aversion of wister rat, prove that bupleurum saponin and bupleurum saponin-a have a noticeable inhibition on the over-activity and stabilizing action. An oral medication of 500 mg/kg Sailosaponin and an intra-abdominal injection of A100 mg/kg of soaps into small rats can noticeably extend the sleeping time caused by sodium hexacyclic bitaryl. The latter can also antagonize the excitation caused by methyl propyl aniline, deoxyephedrine, and caffeine. 0.7% bupleurum saponin acts onn the PT2 in the ganglia of snails. 2% bupleurum extracts has a stronger anesthetic action on the ischiadicus nerve separated from a frog, and this action is in the ratio of 1.7 to the potency of 0.5% procaine. From the summation of the two above actions, it can be seen that they have a close relationship with the anti-convulsive action of bupleurum.

(3) Relieving Pain: The tail pressing method or the acetic acid-produced method can prove that an oral intake of crude bupleurum saponin can relieve pain. The electric shock of rats' tail experiment proves that 478 mg/kg (¼ $LD_{50}$) bupleurum saponin can increase the pain threshold. An intra-abdominal injection of 50 mg/kg or 100 mg/kg crude bupleurum saponin-a and syrup residues can inhibit the twisting reaction of small rats caused by acetic acid and the syrup residues can relieve the pain caused by the pressure method. Some people believe that bupleurum saponin can also relieve pain by means of the tension of smooth muscles.

(4) Relieving coughing: Saikosaponin and bupleurum saponin-a have a stronger action of relieving coughing. The mechanical stimulation of coughing proves that for an intra-abdominal injection of Saikosaponin, the ED50 for relieving cough is 9.1 mg/kg and its effect is close to the effect of 7.6 mg/kg codeine phosphate. The effect of relieving coughing of bupleurum saponin-a is related to its dosage. An intra-abdominal injection of 100–200 mg/kg to wister rats has the most noticeable coughing-relieving action.

Functions and Indications

It expels the external symptoms and reduces the heat. It removes the obstructions of the liver and expels the evil. It strengthens the yang. It primarily treats cold and fever, malaria, liver pains, breast swelling, menstrual irregularities, prolapse of the rectum as a result of the deficiency of qi, prolapse of the uterus, and prolapse of the stomach. It can clean the body, expel the external symptoms, and expel the heat.

1. Fructus Forsythiae

Chemical Composition:

Its fruits contain esters such as forsythin (phillyrin), phillygenin, pinoresinol, pinoresinol-β-D-glucoside; ketones such as rutin; phenyl ethane compounds such as forsythoside-a, forsythoside-c, forsythoside-d, forsythoside-e, suspensaside, and salidroside; ethyl cyclic-hexatone derivatives such as cornoside, rengyol, isorengyol, rengyoxide, rengyolone, rengyoside-a, b, c; Triterpenes compounds such as betulinic acids, oleanolic acids, mrsolic acids, β-amyrin acetate, isobauerenyl acetate, 20 (S)dammar-24-ene-3 β, and 20-diol-3-ace-tate.

Functions and Indications:

It reduces fever, detoxifies, expels swelling, and disperses blood clotting. It primarily treats influenza caused by hot wind, illnesses related to body temperature, heat-induced anuria, carbuncles and poisoning, and gnarls and throat paralysis. It can clear away heat and detoxify. It is the treatment for the internal and external symptoms of heat-induced illnesses for body organs, qi, and blood.

I. Herba Schizonepetae

Chemical Composition:

Its parts above the ground, grains and stalks contain 1.12%, 1.69%, and 0.6% of volatile oil respectively. Its major contents are pulegone, menthone, isomenthone and isopulegone; 1-ethoxypentane, 3-methylcyclopentanone, 3-methylcyclohexanone, benzaldehyde, 1-cten-3-ol, 3-octanone, 3-octanol, cymene, limonene, neomenthol, menthol, piperitone, piperitenone, humulene, caryophyllene. The volatile oil of its parts above ground contains β-pinene, 3,5-dimethyl-2-cyclohexen-1-one, ethenyl dimethyl bezene, cineole, carvone, dihydrocarvone, and verbenone. The infloresence of its grains contains Monoterpene compounds, ketones, and phenol acids.

Pharmacology:

1. Relieving fever and antipyretic action:

An injection of the decoction or extracts of 2 g./kg (crude herbs) herba schizonepetae into the stomach has a mild effect on the rabbit's pyrexia caused by mixed typhoid vaccine. An intra-abdominal injection of 4.4 g/kg dried herba schizonepetae decoction has a noticeable effect on the rabbit's pyrexia caused by the mixed typhoid, paratyphoid, and tetanus vaccine. Ethyl ester herba schizonepetae extracts occasionally have a slight effect on the pyrexia of small rats, which has been treated with endotoxin. An injection of 0.5 ml/kg herba schizonepetae volatile oil into the stomach has an effect on the pyrexia of normal wister rats. One hour after the injection, the body temperature decreases gradually. After three hours, the body temperature is reduced by 2.2° C. in comparison to the body temperature before taking the medication. This indicates that the volatile oil of herba schizonepetae can reduce normal body temperature.

2. Tranquilizing action: An intra-abdominal injection of 0.5 ml/kg of the decoction of herba schizonepetae reduces the activities of rabbits. The muscles of limbs relax, indicating there is a tranquilizing effect.

2. Relieving pain: 15 ml/kg of the decoction of herba schizonepetae is injected into the stomach. After one hour, the heat board method of small female rats increases the pain threshold by 200%. After four to five hours, the pain threshold is increased by 300%. An injection of herba schizonepetae oil into the stomach has no noticeable effect on the latency period of pain caused by the heat board. Methol, the major ingredient of herba schizonepetae, is injected into the stomach and has a 41.3% inhibitory rate on the acetate acid-induced twisting reaction of small rats. Its intensity is similar to that of amidopyrine.

3. Anti-inflammation: An intra-abdminal injection of 20 g/kg decoction of herba schizonepetae has a significant inhibitory effect on the inflammation caused by croton oil inflammation-inducing agent, which is pasted onto the ears of small rats. An intra-abdominal injection of 14 g/kg herba schizonepetae decoction has an inhibitory effect on the increase in the blood capillary permeability caused by an intra-abdominal injection of 0.7% 10 ml/kg acetic acid to a small rat. Pulegone, the volatile oil of herba schizonepetae, is injected into the stomach and this has a 39.8% inhibitory rate on abdominal osmosis. Its anti-inflammation action is similar to that of amidopyrine. 3-octanol and β-pipene have inflammation action.

4. Expeling the phlegm and anti-asthmatic action: From an injection of 0.5 ml/kg herba schizonepetae oil to the stomach or an intra-abdominal injection of 0.25 ml/kg herba schizonepetae oil, the phenol red test of small rats show that herba schizonepetae oil can expel phlegm. Herba schizonepetae oil can directly relax the smooth muscles in the trachea of wister rats and its minimum effective concentration is 0.1 mg/ml. Herba schizonepetae oil can antagonize the contraction of smooth muscles in the trachea by acetycholine or histamine. A spray or an injection in the stomach can extend the asthma latency period of wister rats caused by a mixture acetycholine and histamine and can reduce the occurrence of convulsions.

5. Effects on the immunity of organisms Herba schizonepetae oil has an inhibitory action on the release of slow-reactive-substance A (SRS-A) in the smooth muscles of wister rats, and can directly antagonize the contraction of ileum of wister rats caused by SRS-A indicating that it has an antagonistic action on SRS-A. An injection of 0.3 mg/kg.d herba schizonepetae oil into the stomach at one time or continuously for three days has an inhibitory action on passive skin allergy reaction (PCA) of wister rats.

6. Anti-bacterial action: The decoction of herba schizonepetae has a greater anti-bacterial ex-corporeal action on staphylococci aureus, staphylococci epidermidis, bachillus Finkler-Prior, bacillus bronchisepticus, bacillus diphtheriae. It also has a certain anti-bacterial action on bachillus anthracis, streptococci B, bachillus sanguinis typhi, bachillus dysenteriae, and bachillus pyocyaneus. Its 100% infusion in a test tube has a different degree of inhibition on bachillus dysenteriae, bachillus Finkler-Prior, bachillus pneumoniae, bachillus sanguinis typhi, *Escherichia coli.*, and staphylococci aureus. In the sodium Kirchner medium A culture, herba schizonepetae decoction can antagonize bachillus tuberculosis. Its effective concentration for inhibiting bachillus tuberculosis is 1:100. The decoction of 50% bachillus tuberculosis 0.1 ml is injected into the urinary bladder, this has a significant inhibitory action on influenza virus $A_3$.

Functions and Indications:

It expels wind, expels external symptoms, erupts rashes, and stops bleeding. IT primarily treats influenza, fever, pains, eye itches, coughing, sore throat, measles, urtica, and carbuncles. It expels wind, causes a moderate amount of sweating, and promotes excretion.

II. Flos Lonicerae Japonicae

Chemical Composition:

It contains chlorogenic acid, isochlorogenic acid, ginnol, β-sitosrol, sitgmasterol, and β-sitosrol, sitgmasterol-D-glucoside. It also contains volatile oil, which contains linalool, cis-6.6-trimethyl-2-vinyl-5-hydroxy-tetrahydropyran, ethlpalmitate, 1,1'-bicyclohexyl, methylinoleate, 3-methyl-2-(2-pentenyl), tran-tran-farnesol, ethyllinolenate, β-cubebene, cis-3-hexen-1-ol, α-terpineol, benzylalcohol, 2-methyl-1-butanol, banztlalcohol, phenethylalcohol, cis-linaloolxide, eugenol, and carvacrrol.

Pharmacology:

1. Anti-bacterial action: Ex-corporeal experiments show that the flos lonicerae japonicae decoction and the alcohol infusion has an inhibitory action on Gram positive bacteria such as staphylococci aureus, staphylococci albus, streptococci haemolyticus, bachillus pneumoniae, streptococci peritonitidis, bachillus sanguinis typhi, bachillus sanguinis paratyphi, Escherichia coli., bachillus dysenteriae, bachillus Finkler-Prior, bachillus tussis convulsivae, and bachillus pyocyaneous, and negative bacteria. The infusion has a stronger action than the decoction. If used together with fructus forsythiae, the anti-bacterial range can also complement each other. If used together with penicillin, it can increase the anti-bacterial action of penicillin on staphylococci aureus. There are no consistent findings on the sensitivity of these bacteria. Generally speaking, it has a stronger action on salmonelleae, especially bachillus sanguinis typhi and bachillus sanguinis paratyphi. A high concentration of flos lonicerae japonicae can inhibit shiga's bacillus. A low concentration of flos lonicerae japonicae can inhibit shiga's bacillus/shigella dysenteriae, followed by schmitz's bacillus. It has almost no effect on Flexner's bacillus. The decoction, infusion, and extracted liquor of flos lonicerae japonicae, by means of board drilling method, has a stronger germicidal and antibacterial effect on bacillus caries-streptococci Finkler-Prior. Its anti-bacterial action increases with concentration. Its anti-bacterial effect is the best for extracted liquor, followed by decoction. The decoction of flos lonicerae japonicae in the ratio of 1:20 cultured in the epithelial cells of the nephron of the embryo, can have an inhibitory action on influenza virus and herpes. It can inhibit the replication of viruses, and retard the pathological changes caused by the viruses. Flos lonicerae japonicae can inhibit Sachs Disease.

2. Anti-toxicity: An intra-abdominal injection of 7.5 g/kg flos lonicerae japonicae can make the $LD_{50}$ of the bachillus pyocyaneous endotoxin or the survival rate of small rats with bachillus pyocyaneous to be over 50%. An intravenous injection of 6 g/kg flos lonicerae japonicae distilled solution has a therapeutic effect on the rabbits with the bachillus pyocyaneous endotoxin and can improve the reduction of white blood cells and anti-pyrexia so caused.

3. Anti-inflammation and antipyretic action: An intra-abdominal injection of 0.25 g/kg flos lonicerae japonicae extracted solution can inhibit the swelling of feet of wister rats by chondrus ocellatus and can also inhibit the swelling of feet caused by egg serum. An intra-abdominal injection of 8 g/kg of flos lonicerae japonicae extracted solution twice daily continuously for six days can inhibit the osmosis of croton oil granuloma and the formation of granulation.

4. Action on the immune system: Ex-corporeal experiments of the flos lonicerae japonicae decoction in the ratio of 1:1280 can still promote the phagocytosis of white blood cells. An intra-abdominal injection of flos lonicerae japonicae extracted solution to small rats can promote the phagocytosis of inflammation cells. 250 mg/kg flos lonicerae japonicae decoction can reduce the positive percetnage of the α-ANAE in the T-cells of wister rats, indicating that itt can inhibit the immunity of cells.

Functions and Indications:

It clears away heat and detoxifies eliminates carbuncles and expels swelling, and cools the blood and fights against diarrhea. It primarily treats fever caused by hot wind, diarrhea caused by hot wind, carbuncles and acne, throat paralysis, and other infectious illnesses. It can also clear away heat and detoxifies. It is a treatment for both the internal and external symptoms in qi and blood.

V Calculus Bovis

Chemical Composition:

It contains bilirubin, bile acid (consisting of cholic acid and deoxycholic acid), bile salts, cholesterol, ergosterol, fatty acids, lecithine, Vitamin D, and inorganic elements such as calcium, sodium, iron, potassium, copper, magnesium, and phosphorus. It also contains para-carotene and amino acids such as alanine, glycine, taurine, aspartic, arginine, leucine, and methionine, and two peptides, namely, SMC-S2 and SMC-F, substances for the contraction of smooth muscles.

Pharmacology:

1. Action on the central nervous system:

(1) Tranquilizing action: *Calculus bovis* has an antagonistic action on the excitation of the central nervous system of small rats caused by caffeine, camphor, and cepharathin. It can also increase the tranquilizing action of chloral hydrate, urethane, or sodium barbital. Taurine has a directing action on the central nervous system, can reduce the combined action of spontaneous activities and pedaling activities of small rats, and increase the hypnotizing action of sub-threshold pento-barbital sodium of small rats. The electrophoresis of the cerebral cortical nerves prove that taurine can inhibit both the spontaneous and induced electrical activities and produce hyperpolarization. It is the same as the inhibitory effect of the central nervous system after the administration of the pharmaceuticals. Besides, the inhibitory effect of taurine on the spinal cord and brain stem is antagonized by strychnine. From this, it is possible that taurine is an inhibitory neurotransmitter and acts through corresponding receptors or γ-GABA receptors. The central nervous system can also have taurine neurons. But some experiments prove that taurine has no significant affinity for post-synaptic GABA receptors and cannot replace the inhibitory effect and modulating effect of GABA on the central nervous system.

(2) Anti-convulsive action: It is written, "Calculus bovis primarily treats convulsion, cold heat, and intense heat." Experiments prove that a daily oral intake of 1 g/kg calculus bovis to small rats continuously for six days can antagonize the convulsion caused by caffeine and cocaine and alleviate the small rats' convulsion caused by camphor and cepharathin, but is not effective to the convulsion caused by strychnine. It is also reported that taurine can significantly extend the latency period of the convulsion of small rats caused by strychnine. Taurine has an inhibitory effect on the convulsion caused by pento-tetra-amine, cepharathin, carbon monoxide, aluminum oxide, 4-amino pyride, penicillin, highly pressurized oxygen, a lack of oxygen, a low concentration of calcium, source of sound, and L-uric acid.

(3) Antipyretic action: Calculus bovis has no effect on the antipyretic action of normal wister rats, but can inhibit the fever caused by 2,4-di-nitrophenol. Calculus bovis has no noticeable antipyretic effect on the rabbits' fever caused by mixed typhoid and paratyphoid vaccine. Studies of the antipyretic mechanism of calculus bovis reveal that the 5-HT within the exhausted brain can noticeably antagonize the antipyretic effect of taurine. An injection of taurine into the hypothalamus of wister rats can increase the body temperature of wister rats, but can reduce the body temperature instead if a large dosage is administered. Strychnine can antagonize pyrexia. This indicates that taurine in the hypothalamus can act as a medium to regulate body temperature. The antipyretic action for a larger dosage of taurine may be due to the fact that taurine is transmitted and this produces temperature regulation in other related brain parts. An injection of taurine into the cerebral ventricles can inhibit the heat-induced pyrogenesis of endotoxin and white blood cells. After the termination of the medication, heat is produced again. But so such effect occurs to the heat inhibitory mechanism of the prostate gland E1 (PGE1) and prostate gland E2 (PGE2).

(4) Pain alleviation: An oral intake of calculus bovis to small rats does not produce noticeable pain relief. But an oral intake or an injection of taurine does not produce noticeable pain relief.

2. Action on the cardiovascular system: Calculus bovis, cholic acid, and bilirubin have a cardiac tonic effect on the heart separated from frogs, wister rats, or rabbits. From the infusion experiments of the ears separated from rabbits, it is proved that calculus bovis can dilate blood vessels. Calculus bovis and cholic acid have a contracting effect on the aortic arteries of wister rats whereas bilirubin has a weaker contracting effect on the aortic arteries of wister rats. When wister rats suffering from organic or kidney-induce(i hypertension are orally administered with 100 mg/kg calculus bovis or calcium cholic acid, they will have a significant and long-lasting blood pressure lowering effect, with a hypotensive value of 5.32~6.65 kPa (40~50 mmHg) for one day or more. An intravenous injection of calculus bovis to an anesthetized rabbit has a long-lasting hypotensive effect. From the experiments of anemia in the formation of thrombi and blood clotting in dispersed blood vessels, it is found that the group taking calculus bovis (30 mg/kg) can inhibit the reduction of heart pulse and the reduction of blood platelets, and inhibit the formation of hemorrhagic dead cells, indicating that calculus bovis has an agnostic effect. Calculus bovis contains taurine. Cardiac muscles also contain plenty of taurine. When the amount of calculus bovis in the cardiac muscles reduces, taurine can have an agnostic effect for treating heart functions. Taurine can treat heart failure. A long-term oral intake of taurine can prevent the accelerated hemorrhagic heart failure caused by incomplete opening and closing of aortic valves. This extends the life expectancy of rabbits. The heart-failure mortality rate of the treatment group significantly reduces with a lower heart pulse. The maximum acceleration in the movement of the left ventricles is significant. Taurine does not affect the normal rate of rabbits and the final diastolic pressure of left ventricles, but significantly increase the output and systolic pressure of the left ventricles. After administering 1 mg/kg propranolol or diltiazem, the calcium antagonist, to rabbits, the output of the left ventricles reduces whereas taurine can improve the output of left ventricles. From the results of the clinical double-blind treatment for hemorrhagic heart failure, it is found that the treatment group (a daily intake of 6 g. taurine for four weeks) produces a noticeable treatment effect, and does not affect the action and metabolism of cardiac tonic such as catecholamines and digitalis.

Ex-corporeal experiments of taurine clearly show that the inhibition of ADP, arachidonic acids and collagen promote the agglomeration of blood platelets and produce the dosage-dependence relationship. In the ex-corporeal experiments, it is also clearly shown that there is the inhibitory action on the agglomeration of blood platelets. Taurine has no effect on the formation of TXA by arachidonic acids, but can inhibit the formation of TXA by collagen. The inhibition in the release of arachidonic acids further inhibits the formation of TXA because of its anti-blood platelets agglomeration mechanism. Taurine has no noticeable effect on the formation of prostate glandis (PGI), but has a noticeable inhibition on the formation of thrombi by means of the mixture of ADP and collagen adrenaline. Taurine can significantly inhibit myocardial blood deficiency and damage. It has a stabilizing effect on the cell membrane and prevents the pbospholipids in the cell membrane from being disintegrated. It can regulate the ion permeability of the cell membrane and antagonize the myocardial injury caused by hyperpolarization of calcium. Taurine can also reduce the formation of oxygen free radicals and increase the formation of glutathione. It also increases the excretion of oxygen free radicals and reduces its injury to myocardia.

Taurine can prevent cardiac arrhythmias and the antagonistic effects of cardiac arrhythmias by disopyramide, propafenone, barbital sodium, verapamil, and $\beta$-receptor blockers. Taurine and quinidina when used together have a better anti-arrhythmic effect of small rats. Taurine has a biphasic moderation in the $Ca^{2+}$ in the myocardia. It can also play an important role in the poor anti-cardiac arrhythmic mechanism. Some people also consider taurine fights against cardiac arrhythmias because it acts on the cell membrane of the myocardia and regulates the $K^+$ permeability of the cell membrane, preventing the loss of $K^+$. Some people also think that taurine can pass through the $\alpha$-receptors, which block myocardia. The effective anti-arrhythmic content of calculus bovis is taurine.

Taurine has a hypotensive effect for wistser rats suffering from essential hypertension or mister rats suffering from deoxy-cortisone acetate-induced hypertension. Its hypotensive mechanism may be due to the fact that its property of inhibiting the activity of the sympathetic nervous system by neurotransmitters or neural moderators activate endogenous opioid peptide substances, thus reducing blood pressure. Some people also think that the hypotensive effect of taurine is related to the the central adrenaline—vasopressin system. When using taurine to treat essential hypertension and critical hypertension, the effects are satisfactory. Besides, taurine can reduce blood cholesterol, increase high-density lipoproteins, and prevent atherosclerosis.

2. Choleretic action and the protection for experimental liver injury: An oral intake of 100 mg/kg calculus bovis for wister rats can relax the dilators in the bile duct and promote the excretion of bile. From the test on the separated gall bladder and whole bile duct specimen, the smooth muscle contracting factor (SMC) of calculus bovis makes the smooth muscles of the gall bladder and the dilator in the opening of the bile duct contract and thus inhibit the excretion of bile. But most of the choleretic acids, especially deoxy choleretic acid, can relax the dilators of the bile duct, and produces a choleretic action. These two types of antagonists form the moderating mechanism of the excretion of bile in organisms. Taurine provides the protection for the liver injury caused by carbon tetrachloride and inhibits the rise of ALT so produced. Pathological sectioning shows that taurine can promote the repairing of liver cells and the prevention of lipohepatitis.

3. Effects on immune functions: An infusion of 100 mg/kg natural or man-made calculus bovis can noticeably increase the function of macrophages in the abdomens of small rats. An intra-abdominal or intra-muscular injection can also have such an action. An infusion of 100 mg/kg natural or man-made calculus bovis can noticeably increase LPS to stimulate the conversion of lymphatic cells. It does not produce a significant action on the promotion of the AconA. This may indicate that it is due to the moderating mechanism of the mononeuron macrophages or B cells. Therefore, taurine produces its immunological pharmacological action. This action may be related to its antipyretic and detoxifying effects.

4. Toxicity: Infuse 7.5 g/kg of calculus bovis into the stomach of small rats. After four hours, repeat the above process once. The activities of the majority of animals become noticeably reduced after taking the medication. They lie down together and scarcely move. Their normal activity level is restored after three hours. They are observed for seven days and no toxic reactions occur. None of these ten animals die. The $LD_{50}$ for an intra-abdominal injection of calculus bovis is 479.8 m/kg. The $LD_{50}$ for an injection of the calculus bovis within the gall bladder in cows and the calculus bovis cultured in the gall bladder is 497.5 mg/kg and 442.6 mg/kg respectively. These are similar to natural calculus bovis. For an oral intake of 0.6 mg/kg calculus bovis of small rats, no weight loss and other symptoms can be observed for six days. A daily oral intake of 0.1 g/kg calculus bovis for hypertensive wister rats continues for fifteen days, and no major pathological changes can be observed in major body organs.

The $LD_{50}$ for infusing chloretic acid to the stomach of small rats is 1.52 g/kg whereas that of the deoxy-chloretic acid is 1.06 g/kg. The $LD_{50}$ for an intra-abdominal injection of taurine to small rats is 6.63+/10.4 g/kg whereas that for an intravenous injection is 0.33 g/kg. The $LD_{50}$ for an intravenous injection of deoxy-chloretic acid is 0.15 g/kg, For an infusion of 4 g/kg taurine to small rats, no pathological changes are found in these twenty animals for three days. The substitutes for natural calculus bovis are primarily the cultured calculus bovis and man-made calculus bovis. Experiments show that both natural calculus bovis and cultured calculus bovis have tranquilizing, anti-inflammatory, and antipyretic actions. These two have better quantity-potency relationship at a dosage of ½~¼ $LD_{50}$ and the intensity of their pharmacological effects is similar. Their anti-convulsive, cardiac tonic, hypotensive action, and toxicity are similar. The intensity of the anti-convulsive, sleep-promoting, cardiac tonic, and antipyretic actions of man-made calculus bovis is greater than that of natural calculus bovis and cultured calculus bovis, but is not so good as them in their anti-convulsive actions of the intestines separated from bodies. The anti-convulsive action of new man-made calculus bovis is stronger than that of man-made calculus bovis. The new formula for man-made calculus bovis—agent B is better than calculus bovis and man-made calculus bovis in the anti-inflammatory, sleep-promoting, anti-convulsive, and antipyretic action, but its anti-anemic and ALT reducing action is better than that of man-made calculus bovis.

Functions and Indications:

It clears away heart-fire and cools the liver. It clears away the phlegm and promotes the restoration of special senses. It clears away the heat and detoxifies. It treats heat illnesses, coma, stroke, fright, convulsion, children's sudden fright, sore throat, and blistering in the mouth and tongue. It strengthens the excretion and the clearing of internal heat.

VI. Fructus Arctii

Chemical Composition:

Its fruits contain arctiin, hydrolyzed arctigenin, glucose, amatairesinol, trachelogenin, sesquilignan AL-D and AL-F. Its seeds contain arctiin, lappaol A, B, C, D, E, F, and H. It seeds also contain fatty acids. The composition of the fatty acids is arachic acid, stearic acid, palmitic acid, and linoleic acid.

Pharmacology:

1. Anti-bacterial and anti-viral action: The infusion of fructus arctiin in a test tube has an inhibitory action on nine types of fungi such as violaceus.

2. Hypoglycemia: Extracts of fructus arctii can reduce blood sugar concentration or wister rats for a long period of time, and can increase the tolerance of carbohydrates. Normal small rats are fed with a diet containing 6.25% fructus arctii or a decoction of fructus arctii for twenty-eight days. It turns out that this does not affect the glucose equilibrium parameter within the body of small rats. Fructus arctii can aggravate the symptoms of diabetes mellitus of small rats, who suffer from streptococci-induced diabetes mellitus.

3. Antagonistic action on calcium: The colon test of wister rats proves that trachelogenin has a noticeable antagonistic action on calcium and has an inhibitory effect on the contraction caused by a high concentration of potassium. The $IC_{50}$ for a concentration of $1.1 \times 10^{-6}$ mol/L and a $pA_2$ of 6.60 is one-sixth of that of the commonly used calcium antagonist such as verapamil. An intra-venous injection of 10 mg/kg of fructus arctii has a noticeable and long-term hypotensive effect for self-induced hypertension.

4. Action on nephrosis: An intra-abdominal injection of amino nucleosid into wister rats causes nephrosis whereas an intra-abdominal injection of arctigenin can inhibit the increase in the excretion of proteins in urine and improve the serum biochemical index, indicating its anti-nephrosis action. An intra-abdominal injection of fructus arctii almost has no effect on the excretion of proteins, but an oral intake of fructus arctii is effective. This may be due to the fact that fructus arctii is hydrolyzed into arctigenin in the digestive tract, and this produces its anti-nephrosis effect.

5. Action against the development of tumor and pathological changes: An anti-pathological change factor separated from fructus arctii has a molecular size of over 300,000. It is heat-resistant, protein-resistant, and is sensitive to MnCl. Methyl dicholoride and ethanol are used to separate a tumor-growth inhibitory substance from the roots of fructus arctii.

6. Growth promotion: Different ratios of natural fructus arctii-containing edible fibers are added to a basal diet containing a toxic level of amaranth. This mixture is fed to weaned wister rats. The growth of wister rats is increased and exceeds that of wister rats, which are fed with a basal diet.

Functions and Indication:

It expels wind heat, releases the inhibited lung energy, erupts rashes, promotes throat, disperses blood clotting, detoxifies, and fights against inflammation. It primarily treats wind-heat cough, sore throat, the inhibition of rashes, wind-heat itching, and swelling and poisoning of herpes and ulcers. This disperses the wind, is mild in nature, produces sweating, and treats the texture of muscles.

Pharmaceutical Methods:

Let 3,000 g. of radix bupleuri scorzonerifolium wild, 2,000 g. of flos lonicerae japonicae, 2,200 g. of fructus forsythiae, 1,900 g. of fructus arctii, 2,800 g. of herba schizonepetae, 100 g. of calculus bovis, and 1,200 g. of suppository exicipient (for example, cocoa butter) be the best schematic illustration of the above-mentioned pharmacological composites. These are first distilled to extract volatile oil, which is then filtered to produce dry infused plaster powder, which is then watered and modeled as the suppository for fever and influenza. The pharmacological process of this suppository for fever and influenza is stated as follows:

Step 1: Add the quantity of water equal to the weight of radix bupleuri scorzonerifolium wild, fructus forsythiae, and herba schizonepetae to the above pharmacological composites, which are infused for two hours. Then add water five times the weight of radix bupleuri scorzonerifolium wild, fructus forsythiae, and herba schizonepetae to the above pharmacological composites to extract 6 ml of volatile oil within a period of four hours. The aqueous solution after distillation becomes approximately 6,000 ml.

Step 2: The above-mentioned gruff obtained after distillation is mixed with flos lonicerae japonicae and fructus arctii, which have infused with water equal to the weight of these composites for one hour. Then add water five times the weight of flos lonicerae japonicae and fructus arctii and decoct the mixture for two hours to obtain approximately 3,000 ml of the first decoction after filtration.

Step 3: Add water four times the weight of the remaining gruff after filtration to this gruff and decoct the mixture for one hour to obtain approximately 20,000 ml of the second decoction after filtration.

Step 4: Mix 56,000 ml of the aqueous solution after distillation in the above Step 1, and the first and the second decoction in Step 2 and Step 3 respectively. Make this solution into concentrated decoction with a relative density of 1.20~1.25 (at 70~80° C.), which is cooled to obtain a concentrated solution of approximately 11,000 ml.

Step 5: To the above-mentioned concentrated solution, add approximately 40,000 ml of 95% ethanol till the alcohol concentration reaches 75%. Stir the solution and let it rest for approximately 24 hours. Then it is filtered and the ethanol is recycled. The solution so obtained is allowed to be concentrated at a low temperature, and dried and powdered to form over 20 mu dry powder extracts. A total amount of approximately 1,000 g of dry powder extracts is obtained.

Step 6: To the above dry infused powder extracts, add approximately 1,120 g. of calculus bovis and volatile oil. Add 1120 g of the suppository exicipient (cocoa butter). Heat the above mixture (at a constant temperature of 60° C. +/− 2° C.) Evenly mix the solution and then water and model it to produce a total number of 1,120 suppositories at the weight of 2 g per suppository.

For patients suffering from general fever and influenza, this suppository for fever and influenza can be applied to the rectum so that it is directly absorbed into the rectum so as to prevent it from the damage of the enzymatic action of livers and reduce the poisonous effects or side effects of pharmaceuticals to the livers with the result that it can rapidly bring down temperature and relieve symptoms of influenza (such as fever, cough, headaches, nasal congestion, sore throat, running nose, sneezing, and aching pains all over the body) with few poisonous and side effects and safety and convenience in using it.

Figure 2:
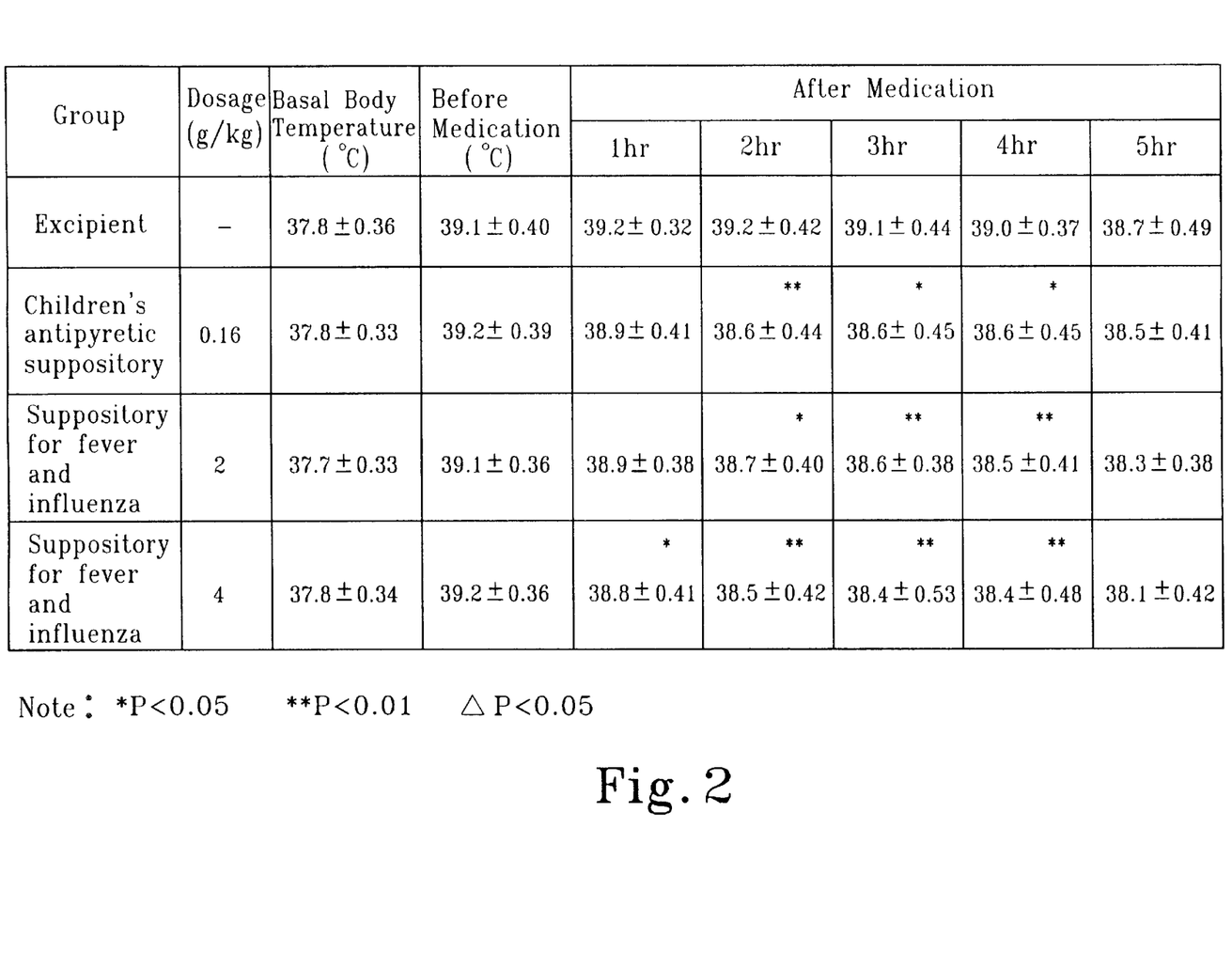
FIG. 2 is a view of the pyrogenic effects of cerevisiae fermentum on the body temperature of wister rats.

Referring to FIG. 2 of the schematic illustration of the pyrogenic effects of the cerevisiae fermentum on the body temperature of wister rats, the above-mentioned pharmacological composites are made into the suppository for fever and influenza following the above steps of distillation, filtration, and watering and modeling. Experimental methods for testing the action of this suppository on expelling heat are stated as follows:

Experimental Materials:

1. The weight of each suppository for fever and influenza is approximately 2 g, which contains 5 g. dried medicinal herbs. 0.5 to 1 g. dried medicinal herbs are clinically used for every kilogram of body weight 2. The excipient of the suppository is the same as the suppository for fever and influenza in the suppository excicipient, but contains no pharmaceuticals.

3. Children's antipyretic suppository is produced by the pharmacological plant in Zhanjiang City, China with a batch number of 950903. Each suppository is approximately 1.3 g. and contains paracetamol. One suppository is administered to the rectum for one to two times daily. Medication is calculated in terms of 15 kg of the child's body weight. 20 mg of paracetamol is medicated to every kg of body weight.

4. Extract a solution of fresh cerevisiae fermentum from a suspension of 10% fresh cerevisiae fermentum and then filter. The gruff obtained after filtration is washed with saline solution for several times. After the gruff has been centrifuged, remove the clear solution on the top. Use 0.5% hydroxyl-methyl cellulose to form 1% solution.

5. Wister rats with a weight of 150 to 200 g. were supplied by the Center for Experimental Animals in the Henan University of Medicine.

Methods and Results:

Choose healthy male wister rats with a weight of 150 to 200 g. Let the wister rats remain in the laboratory for three days so that they can adjust themselves to the laboratory environment. Measure the temperature of their anus once daily with a thermometer. Measure the temperature every two hours for three times daily before the experiment. Select those wister rats with temperature changes not exceeding 0.3° C. A subcutaneous injection of a 10 ml/kg suspension of 10% cerevisiae fermentum is administered to the backs of wister rats. After four hours, the body temperature of wister rats significantly increases. Select those wister rats with temperature rises exceeding over 1° C. Forty wister rats with similar body temperature were randomly assigned to the excipient control group, children's antipyretic suppository group (that is the positive control group), and the two groups, the high-dose and the low-dose suppository for fever and influenza respectively, with ten wister rats per group. For the two groups administered with the suppository for fever and influenza, the suppository is lightly put into the rectum of wister rats.

1.6 g/kg of the suppository for fever and influenza (equivalent to 4 g/kg of crude drugs and is eight times the minimum dosage for clinical use. For the group of low-dosage suppository for fever and influenza, 0.8 g/kg of the suppository for fever and influenza (this amount is equivalent to 2 g/kg of crude drugs and is four times the minimum dosage for clinical use. 0.8 g/kg excipient is administered at the same time to guarantee that the volume of the pharmaceuticals is the same as that of the other three groups.) For the children's antipyretic suppository group, 0.69 g/kg of children's antipyretic suppository is adminstered (this amount is equivalent to 0.16 g/kg of paracetamol and eight times the clinical dosage. 0.91 g/kg excipient is administered at the same time to guarantee that the volume of the pharmaceuticals is the same as that of the other three groups.) 1.6 g/kg excipient is administered to the excipient control group. After medication has been administered, measure the body temperature of the four groups after one hour, two hours, three hours, four hours, and five hours respectively. Experimental results are reported in FIG. 2.

Experimental Results:

The group with high-dose and the group with low-dose suppository for fever and influenza and the children's antipyretic suppository group show a significant or very significant antipyretic effect on the wister rats' fever produced by cerevisiae fermentum. The antipyretic effects of the high-dose and low-dose suppository for fever and influenza are compared with the results of between-groups. The antipyretic intensity of the suppository for fever and influenza is better than that of the children's antipyretic suppository of an equal multiple of dosage (calculated clinically in terms of pharmaceutical multiples). The antipyretic duration of the suppository for fever and influenza is longer than that of the children's antipyretic suppository. After administering medication for six hours, the effect of the group of high-dose suppository for fever and influenza is significantly different from that of the excipient control and also significantly different from that of the children's antipyretic suppository of equivalent pharmaceutical multiples.

Figure 3:
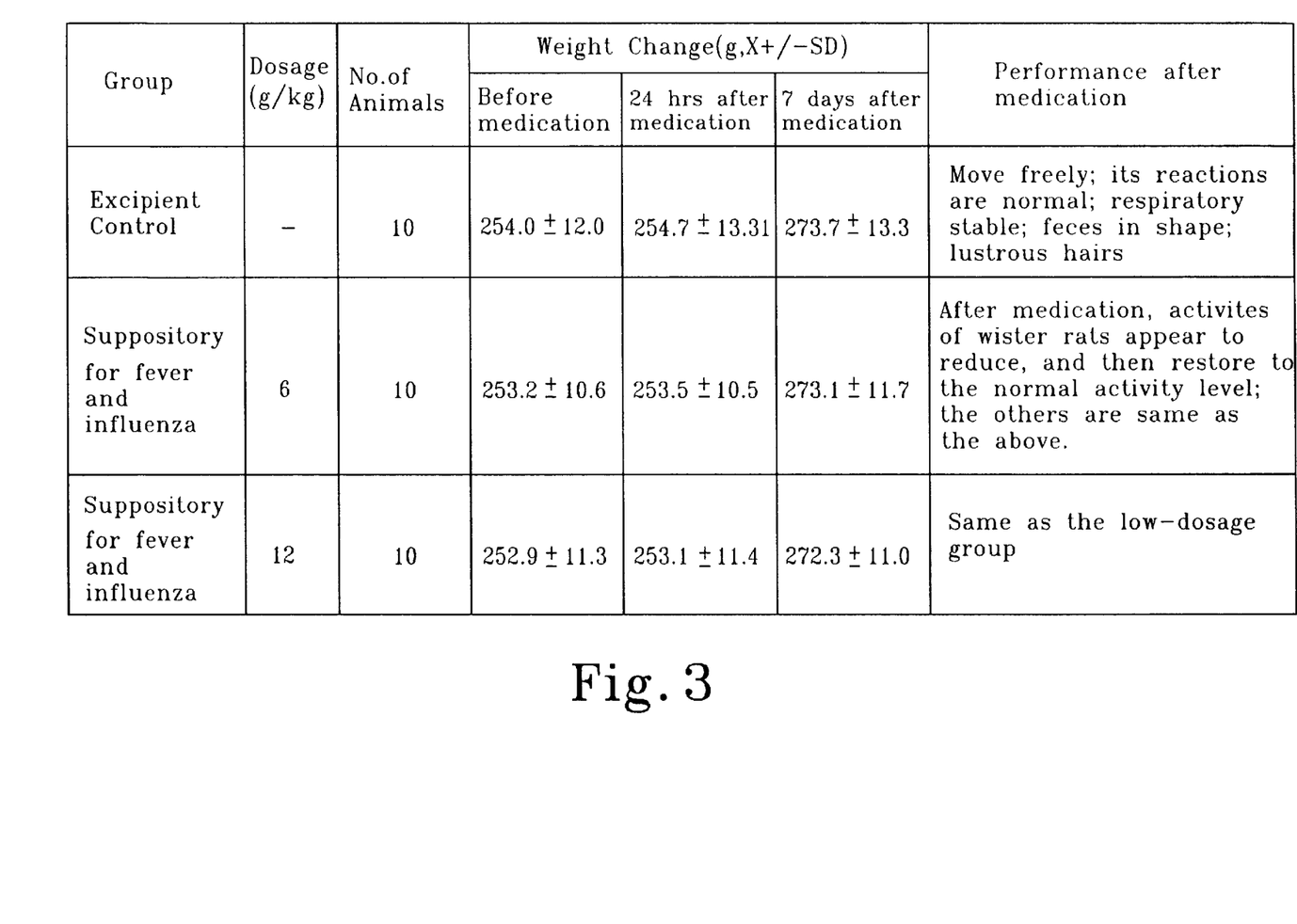
FIG. 3 is a schematic illustration of the toxicological test results of this invention.

Referring to FIG. 3 of the schematic illustration of the pharmacological test results of this invention, it is intended to prove that the suppository for fever and influenza in this invention is a Chinese patent medication of great stability. The toxicology studies in this invention and the experimental methods for testing the stimulation on rectum are stated as follows:

I. Toxicology studies:

1. Each suppository for fever and influenza is approximately 2 g., which contains 5 g. crude drugs. 0.5 to 1 g. crude drugs are clinically used for every kilogram of body weight.
2. The excipient does not contain pharmaceuticals and only constitutes the exicipient of the suppository for fever and influenza.
3. Wister rats with a weight of 230 to 270 g. were supplied by the Center for Experimental Animals in the Henan University of Medicine.

Methods and Results:

Select thirty wister rats with a weight of approximately 250 g. Deprive them of food, but not water, for twelve hours. These wister rats were randomly assigned to three groups. They are the group of high-dose suppository for fever and influenza, the group of low-dose suppository for fever and influenza, and the excipient control group, with ten wister rats per group. These ten wister rats were made up of five male and five female wister rats. For the two groups treated with the suppository for fever and influenza, the suppository for fever and influenza was lightly put into the rectum of wister rats, with an amount of 4 g/kg (equivalent to 10 g/kg of crude drugs) for the high-dose group and an amount of 2 g/kg (equivalent to 5 g/kg of crude drugs) for the low-dose group. 4 g/kg excipient was administered to the excipient control group. After the pharmaceuticals had been in contact with the rectum of wister rats for over four hours, the suppository was administered to the wister rats every six hours for three times daily. 12 g./kg, which is equivalent to 30 g/kg of crude drugs, had been administered to the high-dose group daily whereas 6 g/kg, which is equivalent to 15 g/kg of crude drugs, had been administered to the low-dose group daily. These wister rats were fed under room temperature and observed for seven days. It was found that the feeding, water intake, and the feces and urine of all the three groups were normal. The hairs of these wister rats were lustrous. They increased their weight normally. No wister rats died (Please refer to the figure). After seven days, kill these wister rats and observe with naked eyes their major organs such as hearts, livers, spleens, lungs, and kidneys. The organs of the experimental groups did not exhibit abnormal changes when compared them with the excipient control group. This shows that the maximum tolerance for the rectum medication of the suppository for fever and influenza to wister rats is over 12 g/kg, which is equivalent to thirty times of the maximum clinical dosage of 30 g/kg crude drugs.

II. Rectum stimulation test for the antipyretic suppository:

Experimental materials:

1. Pharmaceuticals: suppository for fever and influenza; exicipient;

2. Animals: healthy adult rabbits with a body weight of 2 to 3 kg were supplied by the Center for Experimental Animals in the Henan University of Medicine Methods and Results:

Take eight rabbits. Deprive them of food for twelve hours. They were then randomly assigned to two groups, that is, the group with the suppository for fever and influenza and the exicipient control group, with four rabbits per group. These four rabbits consisted of two male and two female rabbits. The suppository for fever and influenza was lightly administered to the rectum of rabbits at a dosage of 1 g/kg. An equal dosage of exicipient was administered to the exicipient control group. Allow the suppository or exicipient to be in contact with the mucous membrane of the rectum for over four hours. Separate these rabbits into two groups and kill them at two time slots, that is, after 24 hours and 48 hours respectively. The rectum of these rabbits was observed with naked eyes. It was found that there was no bleeding and swelling in the mucous membrane of the rectum of rabbits for the group administered with the suppository for fever and influenza and the exicipient group. This shows that the rectum administration of the suppository for fever and influenza at a dosage of 1 g/kg (equivalent to 2.5 g/kg of crude drugs and equivalent to the maximum clinical dosage.) does not produce any stimulating effect.

The suppository for fever and influenza has a significant antipyretic action. Its intensity and duration is better than that of the other children's antipyretic suppositories. Besides, toxicity studies show that the rectum administration of the suppository for fever and influenza does not produce any stimulating effect. The tolerance of the suppository for fever and influenza in this invention is over 12 g/kg (equivalent to 30 times of the maximum clinical dosage.) This shows that the suppository for fever and influenza is a Chinese patent medicine of great stability.

Figure 4:
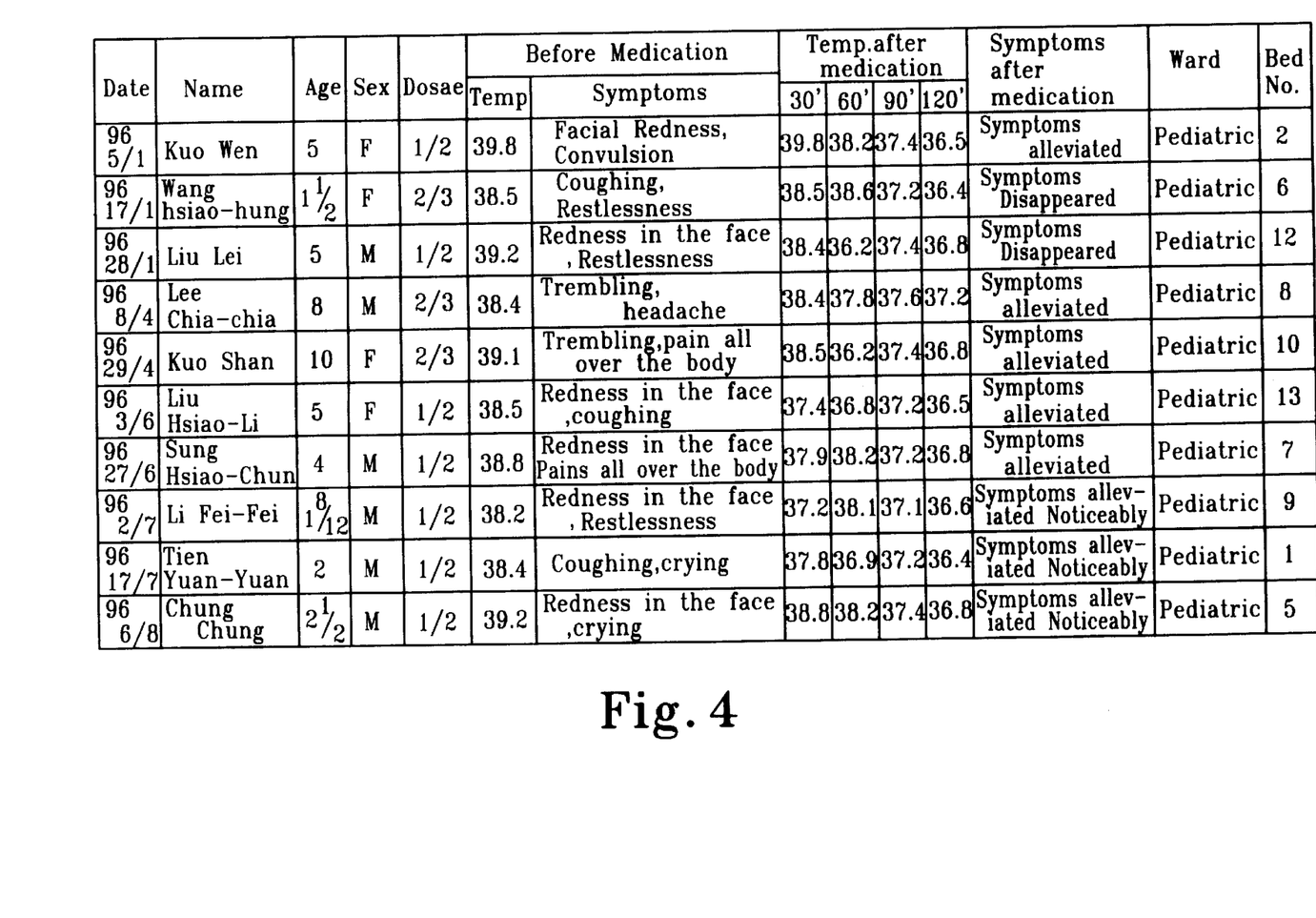
FIG. 4, FIG. 5, and FIG. 6 are the tables depicting the therapeutic effects of this invention.
Figure 5:
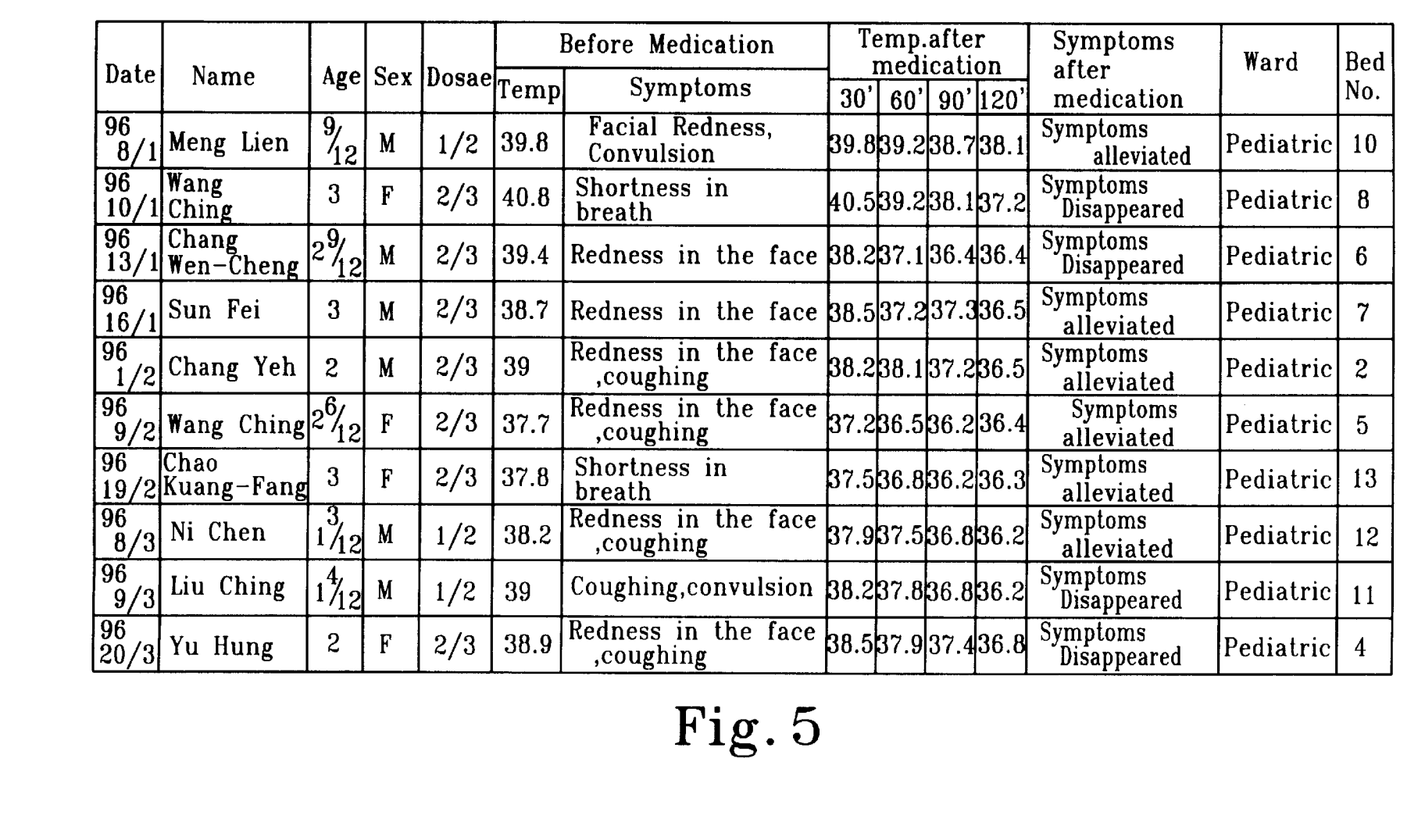
Figure 6:
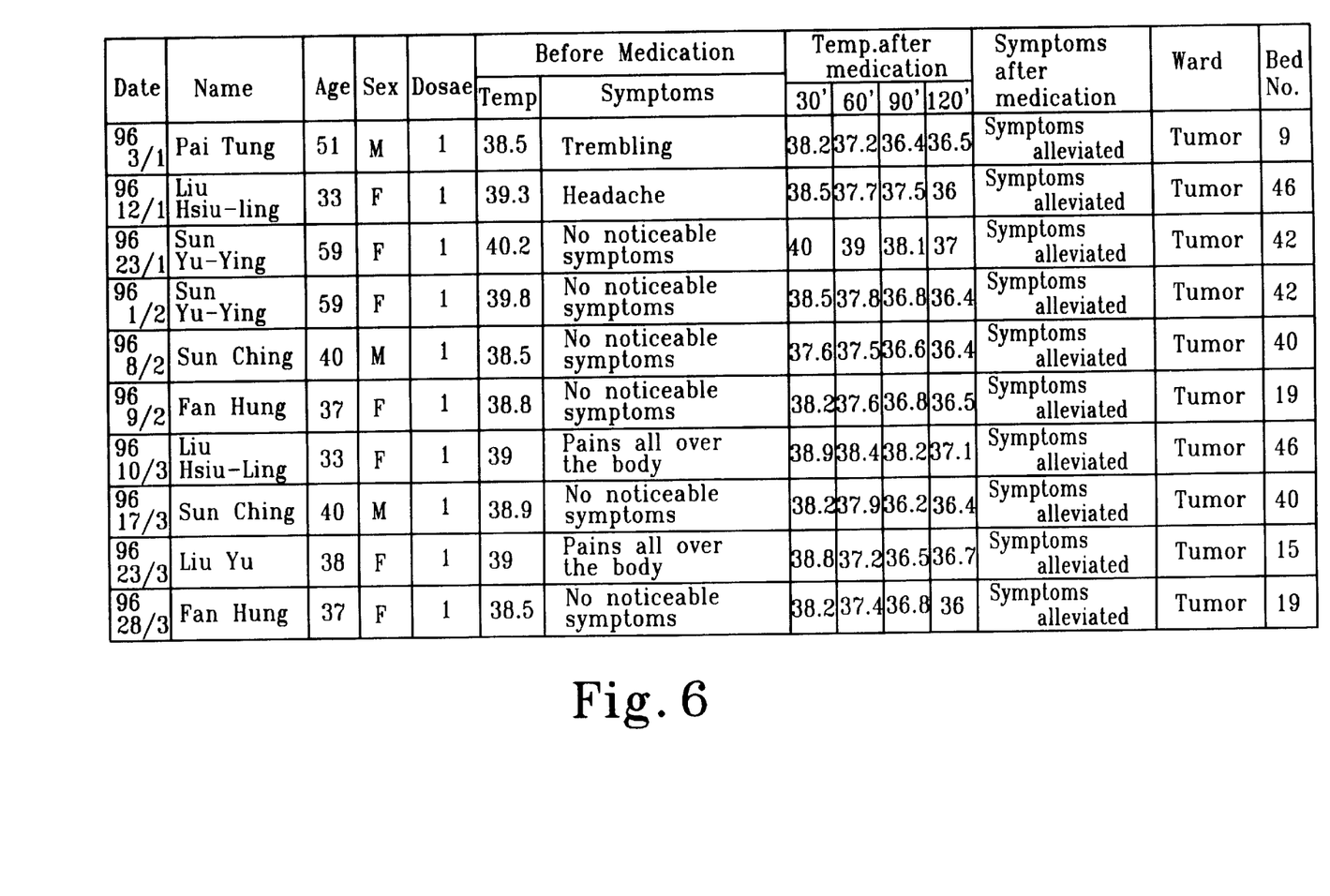

Referring to FIG. 4, FIG. 5, and FIG. 6, they are the tables for the therapeutic effects in this invention. The therapeutic effects of the suppository for fever and influenza of patients of different ages were observed. From these figures, it can clearly be seen that these patients of different ages had noticeable fever (38° C.~40° C.) and other influenza symptoms (such as coughing and sickness all over the body) before taking this medication. But after the administration of different dosages of the suppository for fever and influenza to patients of different ages (one suppository for adults; ½ to ⅔ suppository for children), measure patients' temperature 30, 60, 90, and 120 minutes after taking the medication. From FIG. 4, FIG. 5, and FIG. 6, it can clearly be seen that after taking the medication, patients' high body temperature was rapidly and effectively restored to normal temperature. Besides, influenza symptoms became alleviated or disappeared after taking the medication.

From the above description, it can be readily appreciated that the suppository for fever and influenza in this invention combines all the advantages of chemical pharmaceuticals (western medicine), traditional Chinese medicine to treat fever for common illnesses, expel heat, relieve symptoms of influenza, and physical temperature reduction in an effort to expel all the weaknesses of traditional Chinese medicine, western medicine, and physical temperature reduction, with a low level of toxicity and fewer side effects. While particular embodiment of the present invention has been illustrated and described, it would be obvious to those skilled in the art that various other changes and modifications can be made without departing from the spirit and scope of the invention. It is therefore intended to cover in the appended claims all such changes and modifications that are within the scope of the present invention.

What is claimed is:

1. A pharmaceutical suppository composite for treatment of fever and influenza which comprises 2,750 g to 3,250 g radix bupleuri scorzonerifolium wild, 1,750 g to 2,250 g flos lonicerae japonicae, 1,950 g to 2,450 g fructus forsythiae, 1,650 g to 2,150 g fructus arctii, 2,550 g to 3,050 g herba schizonepetae, 50 g to 550 g calculus bovis, and 870 g to 1,370 g of a suppository excipient.

2. The pharmaceutical suppository composite of claim 1 wherein said radix bupleuri scorzonerifolium wild includes volatile oil wherein said volatile oil contains β-terpinene, limonene, camphene, β-fenchene, pulegone, isoborneol, β-terpineol, linalool, α-copaene, humulene, α-farnesene, aromadendrene, cis-caryophyllene, iso-caryophyllene, β-elemene, γ-muurolene, patchoulane, nootkatone, and ledol.

3. The pharmaceutical suppository composite of claim 1 wherein said radix bupleuri scorzonerifolium wild includes 0.15% saikosaponin wherein said saikosaponin contains bupleurum saponin-a, bupleurum saponin-d, and bupleurum saponin-c.

4. The pharmaceutical suppository composite of claim 1 wherein said radix bupleuri scorzonerifolium wild includes sorbitin, sorbiphenol-7-rhamnosin, quercetin, isoquercetin, isorhamnetin, rutin, and narcissin.

5. The pharmaceutical suppository composite of claim 1 wherein said fructus forsythiae includes esters, ketones, phenyl ethane compounds, ethyl cyclic-hexatone, and triterpenes compounds.

6. The pharmaceutical suppository composite of claim 5 wherein said esters comprise forsythin (phillyrin), phillygenin, pinoresinol, and pinoresinol-β-D-glucoside.

7. The pharmaceutical suppository composite of claim 5 wherein said ketones comprise rutin.

8. The pharmaceutical suppository composite of claim 5 wherein said phenyl ethane compounds comprise forsythoside-a, forsythoside-c, forsythoside-d, forsythoside-e, suspensaside, and salidroside.

9. The pharmaceutical suppository composite of claim 5 wherein said ethyl cyclic-hexatone comprises cornoside, rengyol, isorengyol, rengyoxide, rengyolone, and rengyoside-a, b, c.

10. The pharmaceutical suppository composite of claim 5 wherein said triterpenes compounds comprise betulinic acids, oleanolic acids, mrsolic acids, β-amyrin acetate, isobauerenyl acetate, 20 (S)-dammar-24-ene-3β, and 20-diol-3-ace-tate.

11. The pharmaceutical suppository composite of claim 1 wherein said herba schizonepetae includes volatile oil wherein said volatile oil comprises pulegone, menthone, isomenthone and isopulegone.

12. The pharmaceutical suppository composite of claim 11 wherein said herba schizonepetae comprises 1-ethoxypentane, 3-methylcyclopentonone, 3-methylcyclohexanone, benzaldehyde, 1-cten-3-ol, 3-octanone, 3-octanol, cymene, limonene, neomenthol, menthol, piperitone, piperitenone, humulene, and caryopyllen.

13. The pharmaceutical suppository composite of claim 11 wherein said herba schizonepetae comprises β-pinene, 3,5-dimethyl-2-cyclohexen-1-one, ethenyl dimethyl bezene, cineole, carvone, dihydrocarvone, and verbenone.

14. The pharmaceutical suppository composite of claim 11 wherein said herba schizonepetae further comprises monoterpene compounds, ketones, and phenol acids.

15. The pharmaceutical suppository composite of claim 1 wherein said flos lonicerae japonicae comprises chlorogenic acid, isochlorogenic acid, ginnol, β-sitosrol, sitgmasterol, β-sitosrol, and sitgmasterol-D-glucoside.

16. The pharmaceutical suppository composite of claim 1 wherein said flos lonicerae japonicae includes volatile oil wherein said volatile oil contains linalool, cis-6.6-trimethyl-2-vinyl-5-hydroxy-tetrahydropyran, ethlpalmitate, 1,1'-bicyclohexyl, methylinoleate, 3-methyl-2-(2-pentenyl), tran-tran-farnesol, ethyllinolenate, β-cubebene, cis-3-hexen-1-ol, α-terpineol, benzylalcohol, 2-methyl-1-butanol, banztlalcohol, phenethylalcohol, cis-linalooloxide, eugenol, and carvacrrol.

17. The pharmaceutical suppository composite of claim 1 wherein said calculus bovis comprises bilirubin, bile acid consisting of cholic acid and deoxycholic acid, bile salts, cholesterol, ergosterol, fatty acids, lecithine, Vitamin D, and an inorganic element selected front the group consisting of calcium, sodium, iron, potassium, copper, magnesium, and phosphorus.

18. The pharmaceutical suppository composite of claim 1 wherein said calculus bovis comprises para-carotene and amino acids selected from the group consisting of alanine, glycine, taurine, aspartic, arginine, leucine, and methionine, and two peptides for the contraction of smooth muscles wherein said two peptides are SMC-S2 and SMC-F.

19. The pharmaceutical suppository composite of claim 1 wherein said fructus arctii comprises arctiin, hydrolyzed arctigenin, and glucose.

20. The pharmaceutical suppository composite of claim 1 wherein said fructus arctii comprises amatairesinol, trachelogenin, sesquilignan AL-D and AL-F arctiin, and lappaol A, B, C, D, E, F; and H.

21. The pharmaceutical suppository composite of claim 1 wherein said fructus arctii comprises arachic acid, stearic acid, palmitic acid, and linoleic acid.

22. The pharmaceutical suppository composite of claim 1 in which said excipient is cocoa butter.

23. A method for making a pharmaceutical suppository composite for treatment of fever and influenza comprising the following steps:
   a) adding water to a first mixture containing radix bupleuri scorzonerifolium wild, fructus forsythiae, and herba schizonepetae and distilling the mixture containing said water therein to obtain volatile oil, a post-distillation aqueous solution and gruffs;
   b) mixing said gruffs obtained in step a) with flos lonicerae japonicae and fructus arctii and adding water thereto to form a second mixture and then filtering said second mixture to obtain filtered gruffs and a first decoction;
   c) adding water to said filtered gruffs obtained in step b) to form a third mixture, decocting said third mixture and filtering said third mixture to obtain a second decoction;
   d) mixing said post-distillation aqueous solution obtained in step a) and said first and second decoctions obtained in steps b) and c) to form a fourth mixture, concentrating said fourth mixture to form a concentrated decoction having a density of 1.2–1.25 at 70–80° C. and cooling the concentrated decoction to obtain a concentrated solution;
   e) extracting said concentrated solution obtained in step d) with ethanol to form an extract which is then concentrated and dried to form a dry powder extract;
   f) mixing said dry powder extract obtained in step e) with calculus bovis, said volatile oil and suppository excipients to form a suppository mixture which is then heated and molded to produce said pharmaceutical suppository composite.

24. The method of claim 23 wherein in step a) water is added to said first mixture in two steps with a two hour infusion period between said two steps of adding water; the amount of water added in said first water addition step being equal to the weight of said first mixture and the amount of water added in the second water addition step being five times the weight of said first mixture.

25. The method of claim 23 wherein the step a) includes extraction of said volatile oil from said mixture wherein said volatile oil is extracted after said distilling and within a period of four hours.

26. The method of claim 23 wherein the amount of extracted volatile oil is 6 ml and the aqueous solution after distillation is about 6,000 ml.

27. The method of claim 23 wherein said second mixture formed in step b) is formed with an amount of water equal to the weight of said flos lonicerae japonicae and said fructus arctii and said second mixture is infused for one hour and then distilled to form said first decoction.

28. The method of claim 23 wherein the amount of water which is used to form said second mixture is equal to five times the weight of said flos lonicerae japonicae and said fructus arctii and said second mixture is decocted and filtered.

29. The method of claim 23 wherein filtering said second mixture produces 30,000 ml of said first decoction.

30. The method of claim 23 wherein the amount of water added in step c) is equal to four times the weight of said filtered gruffs and said third mixture is decocted for one hour.

31. The method of claim 23 wherein said second decoction obtained after filtration is 20,000 ml.

32. The method of claim 23 wherein the amount of concentrated solution produced in step d) is 11,000 ml.

33. The method of claim 23 wherein in step e) said concentrated solution is added to approximately 40,000 ml of 95% ethanol until the concentration of ethanol reaches 75% and the ethanol containing solution is maintained for 24 hours.

34. The method of claim 23 wherein said dry powder extract formed in step e) is about 1,000 g.

35. The method of claim 23 wherein the amount of said suppository excipients is equal to the combined weight of said dry powder extract, calculus bovis and volatile oil.

36. The method of claim 23 wherein said suppository mixture is heated to 60° C. +/− 2° C. in step f).

37. The method of claim 23 which produces a total number of 1,120 suppositories wherein each said pharmaceutical suppository composite weighs two grams.

* * * * *